US011694818B2

(12) United States Patent
Riddoch

(10) Patent No.: US 11,694,818 B2
(45) Date of Patent: *Jul. 4, 2023

(54) GENERATOR COLUMNS FOR ELUTION SYSTEMS LOADED WITH PRE-CHARGED MATRIX

(71) Applicant: Jubilant Draximage Inc., Kirkland (CA)

(72) Inventor: Robert William Riddoch, Pierrefonds (CA)

(73) Assignee: Jubilant Draximage Inc., Kirkland (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,494

(22) Filed: Sep. 12, 2022

(65) Prior Publication Data

US 2023/0005637 A1    Jan. 5, 2023

Related U.S. Application Data

(63) Continuation of application No. 16/799,154, filed on Feb. 24, 2020, now Pat. No. 11,443,866.

(51) Int. Cl.
*G21G 4/06* (2006.01)
*G21G 1/00* (2006.01)
*A61L 2/20* (2006.01)

(52) U.S. Cl.
CPC .............. *G21G 4/06* (2013.01); *A61L 2/20* (2013.01); *G21G 1/0005* (2013.01)

(58) Field of Classification Search
CPC ........... G21G 4/06; G21G 1/0005; A61L 2/20
USPC ....... 250/436, 437, 432 pd, 432 R, 432, 433, 250/434, 435
See application file for complete search history.

(56) References Cited

U.S. PATENT DOCUMENTS 11,443,866 B2 * 9/2022 Riddoch .............. G21G 1/0005
2021/0265069 A1    8/2021 Riddoch

* cited by examiner

*Primary Examiner* — Nicole M Ippolito
(74) *Attorney, Agent, or Firm* — BakerHostetler

(57) ABSTRACT

The present disclosure relates in general to nuclear medicine and generators for the production of radiopharmaceuticals for medical use. In particular, present disclosure relates to a generator column that resists high heat such as depyrogenation and sterilization. This allows some steps of the preparation of the column to be performed in a non-sterile environment. This also allows the generator column to be reusable. The present disclosure further describes methods for the preparation of a generator where a parent radioisotope is charged on the column matrix before or after the matrix is loaded in the column.

20 Claims, 2 Drawing Sheets

GENERATOR COLUMNS FOR ELUTION SYSTEMS LOADED WITH PRE-CHARGED MATRIX

CROSS-REFERENCE TO RELATED APPLICATIONS

This application is a continuation of U.S. Ser. No. 16/799,154, filed Feb. 24, 2020 (now U.S. Pat. No. 11,443,866, issued Sep. 13, 2022), the entire contents of which are incorporated herein by reference.

TECHNICAL FIELD

The present disclosure relates in general to nuclear medicine and generators for production of radiopharmaceuticals for medical use. In particular, the present disclosure relates to generator systems having a generator column that tolerates high temperature reached during sterilization, depyrogenation, or both. The present disclosure also relates to generator columns that are loaded with a radioisotope-charged matrix.

BACKGROUND $^{82}$Rb is used as a tracer for positron emission tomography (PET) in the non-invasive determination of myocardial perfusion.

Conventional $^{82}$Sr/$^{82}$Rb elution systems generally comprise a generator system, a saline reservoir, pump system, a valve system, an activity detector, a dose calibrator, a waste container, an infusion tubing assembly, one or more sensors, a computer, and shielded cavities for carrying components of elution system, wherein all components may reside on a platform meant to move the elution system. $^{82}$Rb is generated by radioactive decay of the parent radionuclide ($^{82}$Sr), and its rate of production decreases exponentially through the useful life of the generator. The shelf life of a typical $^{82}$Sr/$^{82}$Rb generator varies from 30 to 90 days. The recharge time between two successive infusions varies from 2 to 16 minutes.

Generator columns used in nuclear medicine are usually made of plastic. Manufacturers prefer to stay away from metallic materials as they may release cations under certain conditions. However, plastic columns are not resistant to high temperature and cannot be easily sterilized. Therefore, when using plastic column, the whole loading process must be made under sterile conditions. Another disadvantage of the plastic columns is that the high level of radiation generated by the radioisotope loaded therein may cause degradation of the plastic material resulting in yellow coloring, deformation and cracks.

There remains an outstanding need for generator columns prepared from materials that avoid the disadvantages highlighted above, and for new processes for the preparation of generator columns.

SUMMARY

The present inventors have identified multiple advantages of non-plastic columns and developed new processes for the preparation of generator columns. For example, the present inventors have developed generator columns for eluting a radioactive solution composed of a radioisotope generated by the columns and an eluant that has eluted through the columns, wherein the columns are made of a material that is a heat resistant material, a radiation resistant material, or both.

A generator column of the present invention is prepared by the steps of:
a) loading the column with a particulate ion exchange matrix; and
b) charging a parent radioisotope on the matrix, wherein the parent radioisotope has the ability to decay into the desired radioisotope.

Alternatively, a generator column of the present invention is prepared by the steps of:
a) loading the column with a first amount of particulate ion exchange matrix;
b) charging a parent radioisotope on a second amount of particulate ion exchange matrix, wherein the parent radioisotope has the ability to decay into the radioisotope; and
c) loading the column with the second amount of charged matrix.

Alternatively, a generator column of the present invention is prepared by the steps of:
a) charging a parent radioisotope on a particulate ion exchange matrix, wherein the parent radioisotope has the ability to decay into a desired radioisotope; and
b) loading the column with the charged matrix.

In an embodiment of the invention, the preparation of a generator column comprises a step of depyrogenation of the column prior to loading the column with any matrix, i.e., the step (b) of loading, and the step (c) of pre-loading, if any.

In an embodiment of the invention, the preparation of a generator column comprises a step of sterilization of the column prior to the step of loading the column. In another embodiment of the invention, the preparation of a generator column comprises a step of sterilization of a column after the step of loading the column, and prior to or after the loaded column is installed in the generator compartment.

In an embodiment of the invention, the preparation of a generator column comprises a step of phosphoric acid treatment of the column prior to loading the column with any matrix, i.e., the step (b) of loading and the step (c) of pre-loading, if any.

In an embodiment of the invention, the preparation of a generator column comprises a step of passivation treatment of the column prior to loading the column with any matrix, i.e., the step (b) of loading and the step (c) of pre-loading, if any.

The term "any matrix" as used herein is intended to refer to a pre-charged matrix or a non-pre-charged matrix.

The order of the steps that are performed prior to the step of loading the column can vary.

In certain embodiments of the invention, the generator column is made of stainless steel, titanium, tin, nickel, cadmium, tungsten, copper, aluminum, or any combination thereof. Preferably, the column is made of stainless steel.

In a preferred embodiment, the parent radioisotope charged on the column is strontium-82, and the desired radioisotope obtained by the decay of the parent radioisotope is rubidium-82.

It is a further object of present disclosure to provide a generator column that is reusable after being used in an elution system for eluting the radioactive solution. According to this object, the used column undergoes a cleaning process that includes the steps of:
a. removing the used matrix from the used column;
b. sterilizing the emptied column resulting from step (a); and c. loading a particulate ion exchange matrix into the sterilized column resulting from step (b).

The present invention further concerns any of the following items:

1. A generator column for eluting a radioactive solution comprising a desired radioisotope that is generated by the column and an eluant that has eluted through the column, wherein the column is prepared by the following steps:
   a. charging a parent radioisotope on a particulate ion exchange matrix, wherein the parent radioisotope has the ability to decay into the desired radioisotope; and
   b. loading the column with the charged matrix resulting from step (a).
2. The generator column of item 1, further including a pre-loading step (c) that is performed before the loading step (b), which comprises loading the column partially with a particulate ion exchange matrix that is not charged with a parent radioisotope.
3. The generator column of item 1, wherein the column is made of a heat resistant material.
4. The generator column of item 3, wherein the heat resistant material has the ability to resist to a heat of about 300° C.
5. The generator column of item 3, wherein the material of the column comprises stainless steel, titanium, tin, nickel, cadmium, tungsten, copper, aluminum, or any combination thereof.
6. The generator column of item 5, wherein the material of the column comprises stainless steel.
7. The generator column of item 1 or 2, further comprising a step of depyrogenation of the column, wherein the step of depyrogenation is performed before any matrix is loaded in the column.
8. The generator column of item 7, wherein the step of depyrogenation comprises dry heating at a temperature from about 210° C. to about 280° C., for a period from about 3 hours to about 12 hours.
9. The generator column of item 8, wherein the temperature is about 210° C. and the period about 3 hours.
10. The generator column of item 8, wherein the temperature is 260° C. ±5° C., and the period is from 3 hours to 6 hours.
11. The generator column of item 1, wherein the particulate ion exchange matrix comprises alpha-stannic acid, zirconium oxide, titanium oxide, aluminum oxide, silica gel, other inorganic, organic ion exchange matrices, or any combination thereof.
12. The generator column of item 1, wherein the parent radioisotope is strontium-82, and the desired radioisotope is rubidium-82.
13. The generator column of item 1, wherein the column has an inlet port, a body, and an outlet port; and wherein the body has a length of about 3.0 cm to about 8.0 cm, an internal diameter of about 4 mm to about 12 mm, and a wall that has a thickness of about 0.4 mm to about 1.2 mm.
14. The generator column of item 1 or 2, further comprising a step of performing a phosphoric acid treatment of the column, wherein the step of phosphoric acid treatment is performed before any matrix is loaded in the column, and wherein the phosphoric acid treatment comprises soaking the column into a phosphoric acid solution having a concentration of about 5% to about 85%.
15. The generator column of item 1 or 2, further comprising a step of performing a passivation treatment of the column, wherein the step of passivation is performed before any matrix is loaded in the column, and wherein the passivation treatment comprises soaking the column into a nitric acid solution, a citric acid solution, or a solution with nitric acid and sodium dichromate.
16. The generator column of item 1, which is installed into a generator compartment, and the generator compartment and the column installed therein are sterilized.
17. The generator column of item 16, wherein the sterilization is performed with steam at a temperature from about 110° C. to about 150° C., for a period is from about 20 minutes to about 60 minutes.
18. The generator column of item 17, wherein the temperature is about 121° C.
19. The generator column of item 1, that was used in an elution system for the elution of the radioactive solution, wherein the column is cleaned by a cleaning process that includes the steps of:
   a. emptying the used column by removing the used matrix therefrom;
   b. sterilizing the empty column resulting from step (a); and
   c. loading a new particulate ion exchange matrix into the sterilized column resulting from step (b).
20. The generator column of item 19, wherein the sterilization step (b) uses steam at a temperature from about 110° C. to about 150° C., for a period of about 20 minutes to about 60 minutes.

DETAILED DESCRIPTION

Figure 1:
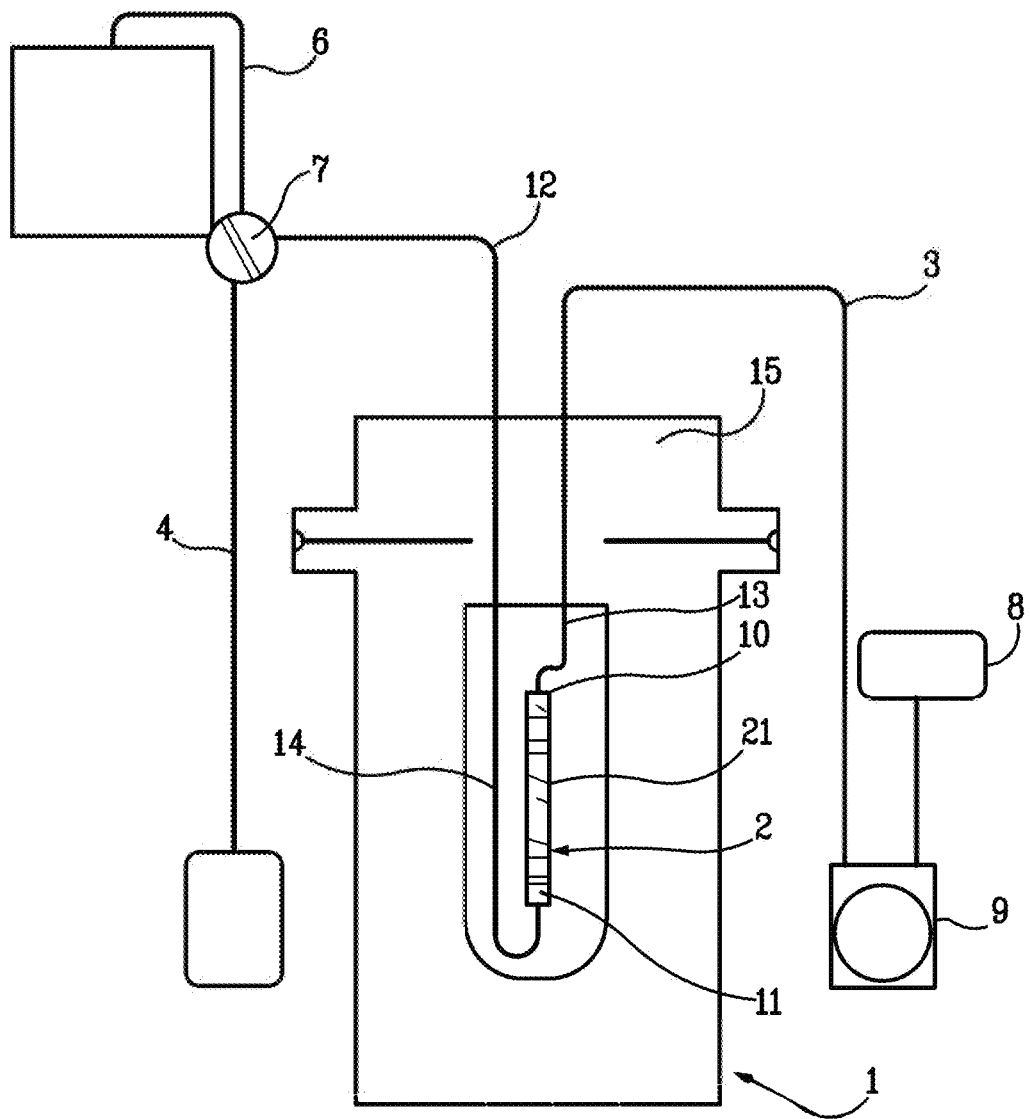
FIG. 1 provides a schematic diagram of an embodiment of the invention where the column (2) is in the generator (1) and is in connection with the elements of the elution system.

The present invention will be more readily understood by reading the following detailed description and study of the included embodiments.

As used herein, the term "column" or "generator column" or "column of generator" refers to the functional component of a Sr/Rb generator that is made up of a heat resistant material, a radiation resistant material, or both, packed with an ion exchange matrix, wherein the ion exchange matrix is loaded or charged with a parent radioisotope such as $^{82}$Sr. Commercial source of $^{82}$Sr may contain $^{85}$Sr as a manufacturing byproduct. According to the present invention, the ion exchange matrix has a higher affinity for the parent radioisotope compared to the daughter radioisotope. Thus, upon elution with a suitable medium, $^{82}$Rb is eluted from generator while $^{82}$Sr and $^{85}$Sr remain adsorbed to the ion exchange matrix. The desired radioisotope $^{82}$Rb is formed in situ by radioactive decay of parent $^{82}$Sr radioisotope in the generator column.

As used herein, the term "generator system" or "generator" or "radioisotope generator" refers to the filled column, wherein a radiation shielding material surrounds the generator column in order to reduce the radiation dose rate at the surface of the generator container, thus protecting the end user. Alternatively, the filled column is installed into a generator compartment that is made of a radiation resistant material or radiation shielding material. In addition to $^{82}$Sr/$^{82}$Rb, parent radioisotopes and corresponding radioisotopes issued from the decay of the parent radioisotopes that can be used with radioisotope generator include, but are not limited to, $^{99}$Mo/$^{99m}$Tc, $^{90}$Sr/$^{90}$Y, $^{188}$W/$^{188}$Re, $^{68}$Ge/$^{68}$Ga $^{42}$Ar/$^{42}$K, $^{44}$Ti/$^{44}$Sc, $^{52}$Fe/$^{52m}$Mn, $^{72}$Se/$^{72}$As, $^{83}$Rb/$^{83m}$Kr; $^{103}$Pd/$^{103m}$Rh, $^{109}$Cd/$^{109m}$Ag, $^{113}$Sn/$^{113m}$In, $^{118}$Te/$^{118}$Sb, $^{132}$Te/$^{132}$I, $^{137}$Cs/$^{137m}$Ba, $^{140}$Ba/$^{140}$La, $^{134}$Ce/$^{134}$La, $^{144}$Ce/$^{144}$Pr, $^{140}$Nd/$^{140}$Pr, $^{166}$Dy/$^{166}$Ho, $^{167}$Tm/$^{167m}$Er, $^{172}$Hf/$^{172}$Lu, $^{178}$W/$^{178}$Ta, $^{191}$Os/$^{1919m}$Ir, $^{194}$Os/$^{194}$Ir, $^{226}$Ra/$^{222}$Rn and $^{225}$Ac/$^{213}$Bi.

In an aspect of the present disclosure, the dimensions of generator columns for use in an elution system are modified relative to conventional columns in order to allow the former to carry a greater amount of ion exchange matrix and higher $^{82}$Sr activity. The enhancement leads to better shelf life and faster recharges between successive elutions of the Sr—Rb generator. In an embodiment, the generator column has a length of about 1.0 cm to about 8.0 cm, an internal diameter of about 4 mm to about 12 mm, and a wall having a thickness of about 0.4 mm to about 1.2 mm. In another embodiment, the generator column has an inlet, a body, and an outlet; and wherein the body has a length of about 3.0 cm to about 8.0 cm, an internal diameter of about 4 mm to about 8 mm, and a wall that has a thickness of about 0.4 mm to about 0.6 mm. In a further embodiment, the generator column has an inlet, a body, and an outlet; and wherein the body has a length of about 4.0 cm, an internal diameter of about 6 mm, and a wall that has a thickness of about 0.5 mm.

The term "about" as used herein preferably refers to ±10% of the values mentioned herein.

As used herein, the phrase "elution system" refers to an infusion system and related components used for generating a solution containing a radioisotope, measuring the radioactivity in the solution, and infusing the solution into a patient. The terms "Sr—Rb elution system" and "$^{82}$Sr/$^{82}$Rb elution system" refer to a strontium-rubidium infusion system and related components used for generating a solution containing rubidium-82, measuring the radioactivity in the solution, and infusing the solution into a patient in order to perform various studies on the patient's heart in particular. More preferably, the elution system comprises a reservoir containing an eluant (preferably sterile saline solution), a pump for pumping the eluant from the reservoir at a desired flow rate through the generator line, a generator valve located on the generator line for proportioning the eluant between the generator and a bypass line that circumvents the generator, a positron detector located on a generator exit line and downstream a merging point where the bypass line merge the generator exit line for measuring the radioactivity of the solution composed of the eluant that has eluted through the generator and the eluant that has transited by the bypass line, and a patient valve for controlling the supply of said solution to a patient outlet and a waste reservoir. The elution system also preferably comprises a controller, which controls the pump and the valves, and receives the data collected by the positron detector.

As used herein, the term "shielded" refers to the condition of being housed within a compartment that is intended to provide shielding to various components of elution system, in order to prevent radiation hazard and exposure of an operator or user to unwanted radiation.

The "shielding" may be made up of a radiation attenuating material that can include, but is not limited to, depleted uranium (DEU), lead (Pb), tin (Sn), antimony (Sb), tungsten (W), bismuth (Bi), any other suitable element or material, or any combination thereof.

In another aspect, the column of the present invention is made of radiation resistant material, which comprises a metallic material, a non-metallic material, or a combination thereof.

In an embodiment of the invention, the column advantageously maintains its physical form and remains substantially unchanged after exposure to a high radiation field for a long period of time, such as 30, 45 or 60 days. Exposure to a high radiation field comprises exposure from 1 mCi to 19 Ci of gamma, beta or alpha radiation. Said exposure may include direct contact with a radioactive source.

In an embodiment, the radiation resistant metallic material comprises stainless steel, titanium, tin, nickel, cadmium, tungsten, tin, copper, aluminum, or any combination thereof. In an embodiment, the radiation resistant non-metallic material comprises PEEK (polyether ether ketone), polypropylene, glass, polytetrafluoroethene (PTFE), or any combination thereof. Preferably, the column is made of radiation resistant metallic material and comprises stainless steel in a major proportion.

In an aspect of the invention, the column comprises pressure-tight seals that can be subjected to autoclave conditions without being damaged.

In an aspect of the invention, the elution system further includes connectors, flanged connectors, "quick connects" such as the DESO Swagelok® quick connects, and attachments for tubing and the generator that are formed from medical-grade stainless steel. The DESO Swagelok® quick connect may contain two O-rings made of Viton® rubber that tolerates high temperature including temperature for sterilization and depyrogenation.

In an aspect of the invention, the ion exchange matrix material comprises inorganic or organic ion exchange matrices. A preferred ion exchange matrix comprises alpha-stannic acid, zirconium oxide, titanium oxide, aluminum oxide, or silica gel, without limitation. Preferably, the ion exchange matrix material comprises alpha-stannic acid. According to an embodiment of the invention, a combination of two or more matrices can be used to load the column.

In another aspect, the amount of ion exchange matrix filled inside the generator column is from about 1 g to about 20 g, preferably from about 4 g to about 10 g, and more preferably from about 5 g to about 7 g, about 6 g±0.2 g, or about 7 g±0.2 g.

In another aspect, prior to being loaded in the column, the ion exchange matrix is preferably washed and decanted with a buffer several times, in order to remove fines. In a preferred embodiment, the matrix is washed and decanted about seven times in a beaker. The buffer is preferably an ammonium hydroxide solution. The ammonium hydroxide solution is in a concentration of about 0.05M to 0.5M, and preferably of about 0.1M. An example of wash and decant procedure is described below in Example 1.

Figure 3:
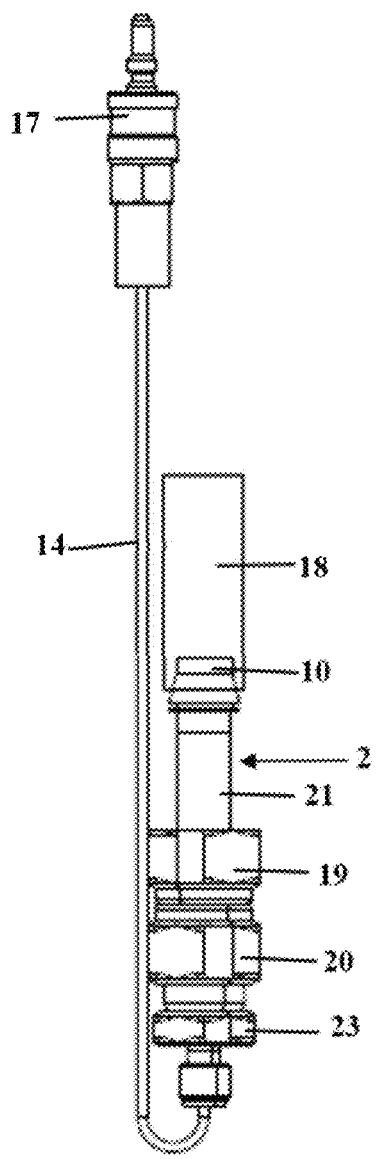
FIG. 3 is a representation of the column (2) of FIG. 2, wherein the inlet tube (13) and the adapter (22) are removed and a filling port (18) is installed on the inlet port (10) to ease the loading of the particle matrix in the column (2).

For loading the matrix in the column, the matrix is preferably wet with the remaining buffer left in the beaker after the last decantation. According to an embodiment, the inlet port (10) of the column (2) is upwardly extended by a funnel or a filling tube (18) as shown in FIG. 3 in order to conduct the matrix in the column. Said funnel or filling tube is preferably made of silicone.

According to a preferred embodiment, a step of measuring the backpressure is performed once the column is filled with the matrix in order to verify the quality of packing of the matrix and the packing consistency between several prepared columns.

In another aspect, after the ion exchange matrix is filled inside the generator column, the matrix is preferably conditioned with the elution of a "relatively concentrated" solution. The elution is preferably made at a slow flow rate during the conditioning step. The flow rate during the conditioning step is preferably of about 0.02-1.0 mL/hour, and preferably of about 0.5 mL/hour. The solution is preferably a buffer or an ionic solution or a solution with a basic pH. For instance, the solution can be a $NH_4OH/NH_4Cl$ buffer, a solution of ammonium hydroxide, or a solution of sodium hydroxide. Preferably, the solution is "relatively concentrated", i.e., between 1M and 3M, and preferably about 2M.

After the conditioning step, a rinsing step is preferably performed wherein the same solution is eluted at a faster flow rate and in a more diluted concentration. For instance, If 2M sodium chloride at 0.5 mL/min is used for the conditioning step, then the rinsing step can be performed by the elution of 0.9% sodium chloride at a flow rate of 10 mL/min. The rinsing step contributes to removing fine particles from the column.

In another aspect, the generator column is loaded with an ion exchange matrix, conditioned and rinsed, and then held (or stored) until being charged with the parent radioisotope.

In accordance with any embodiment disclosed herein, instead of loading completely the column with the full amount of ion exchange matrix, an alternative is to load a partial amount of matrix in the column, and hold or store the column until completion. For example, the column may first be filled at about 50%, 55%, 60%, 65%, 70%, 75%, 80%, or 85% of the total capacity of the column. In accordance with this alternative, completion of the loading can be performed in various ways. One way is to perform the completion by loading the remaining amount of matrix until the column is completely filled, and then charging the parent radioisotope thereon. Another way for performing the completion is by charging the remaining amount of matrix with the parent radioisotope outside the column, and then loading the same in the column. After the remaining amount of ion exchange resin is added to the column, the column may be packed in accordance with the packing step. Thus, any of the generator and elution systems otherwise disclosed herein may be modified so that the column is partially filled with an ion exchange matrix that is free of parent radioisotope, then filled with an additional portion of ion exchange matrix that is pre-charged with the parent radioisotope or not, and then subjected to the loading step.

For charging the parent radioisotope on the matrix that is loaded in the column, the radioisotope is preferably diluted in order to provide the desired concentration in a suitable solution. For instance, a solution of strontium-82 is prepared with 0.1N HCl and Tris buffer. The total amount of strontium is preferably diluted in a solution of 5 mL to 20 mL. Charging the solution of parent radioisotope on the matrix in the column is preferably performed by eluting a solution of parent radioisotope at a very slow flow rate, which is preferably from about 0.5 mL/h to about 5.0 mL/h. For instance, 20 mL of a solution of strontium-82 is preferably charged on the matrix in the column at a flow rate of about 1 mL/h.

After the parent radioisotope is charged on the column, an elution step is preferably performed that can be embodied by an elution wherein the flow rate increases in staircase manner or in a constant manner. As an example, the staircase manner elution step can be achieved by consecutively eluting a) 120 mL of 0.9% NaCl at 1 mL/min, b) 240 mL of 0.9% NaCl at 2 mL/min, c) 240 mL of 0.9% NaCl at 6 mL/min, and d) 360 mL of 0.9% NaCl at 10 mL/min.

In another aspect, provided are elution systems according to any preceding embodiment that further comprise a flow regulator that is set to provide a flow rate of about 10 mL/hour to about 1000 mL/hour, preferably 10 mL/hour to about 100 mL/hour, and more preferably 10 mL/hour to about 60 mL/hour.

In another aspect, a test for generator performance is used to ensure proper column performance during the shelf life of the column.

In another aspect, the generator column is subjected to periodic quality assurance tests. The quality assurance tests are preferably performed on a periodic basis, such as twice per day, once every day, once every two days, once every three days, once every four days, once every five days, once every six days, once per week, once every nine days, once every 10 days, once every two weeks, once every three weeks, or once per month.

In another aspect, the generator column is tested with regard to one or more of trace metals, sterility, radionuclide purity, pyrogens, and pH. Tests for the generator column may include one or more of:
  a. Trace metal analysis by inductively coupled plasma/atomic emission spectroscopy;
  b. Pyrogenic substances test by limulus amebocyte lysate (LAL) test; and
  c. Radionuclide purity test using a multichannel analyzer coupled with intrinsic germanium lithium detector and computer analysis.

In another aspect, a pH probe is preferably installed for online monitoring of the eluate pH.

In another aspect, the generator column can be used to produce a total volume of eluate of about 15 to about 150 liters.

In another aspect, the shelf life of the generator column is at least 20 days, such as about 20 days, 22 days, 24 days, 26 days, 28 days, 30 days, 35 days, 40 days, 45 days, 50 days, 55 days, or 60 days or more.

An aspect of the present invention concerns a generator column for eluting a radioactive solution, which is composed of a radioisotope generated by the column and an eluant that has eluted through the column, and where the column is made of a heat resistant material. A heat resistant material is preferably a material that can resist to the heat of sterilization and the heat of the depyrogenation process. Preferably, the heat resistant material has the ability to provide heat resistance to a temperature of at least 110° C. or at least 210° C. The column is preferably made of heat resistant material. In a preferred embodiment, the column is made of a material that includes a heat resistant material and a radiation resistant material.

In an embodiment of the invention, the generator column can be prepared by the steps of:
  a) loading the column with a particulate ion exchange matrix; and
  b) charging a parent radioisotope on the matrix, wherein the parent radioisotope is a radioisotope that has the ability to decay into a desired radioisotope, which is also called a daughter radioisotope.

In another embodiment of the invention, the generator column is prepared by the following steps:
  a) depyrogenation of the column;
  b) loading the column with a particulate ion exchange matrix; and
  c) charging a parent radioisotope on the matrix, wherein the parent radioisotope is a radioisotope that has the ability to decay into a desired radioisotope.

In another embodiment of the invention, the generator column is prepared by the following steps:
  a) sterilization of the column;

b) loading the column with a particulate ion exchange matrix; and c) charging a parent radioisotope on the matrix, wherein the parent radioisotope has the ability to decay into a desired radioisotope.

In an embodiment of the invention, the generator column can be prepared by the steps of:

a) charging a parent radioisotope on a particulate ion exchange matrix, wherein the parent radioisotope is a radioisotope that has the ability to decay into a desired radioisotope, which is also called a daughter radioisotope; and b) loading the column with the charged matrix.

According to an embodiment of the invention, the radiation resistant material and the heat resistant material comprises stainless steel, titanium, tin, nickel, cadmium, tungsten, tin, copper, aluminum, or any combination thereof. The radiation resistant material and the heat resistant material preferably comprises stainless steel.

Figure 2:
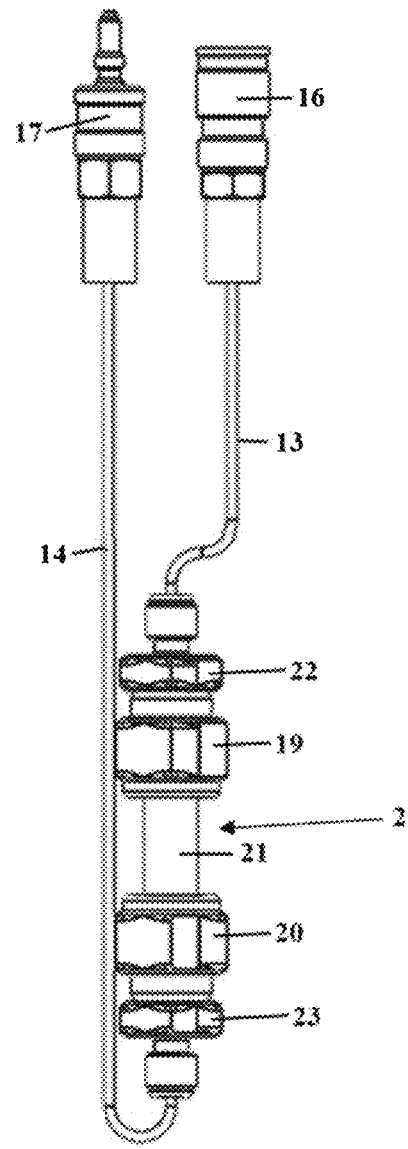
FIG. 2 is a representation of the column (2) in connection with the inlet tube (13) and the outlet tube (14).

In accordance with an embodiment of the invention, which is illustrated in FIG. 2, the column (2) is connected upstream to adapter (22) that enlarges the internal diameter between the tube (13) and the body (21) of the column (2). Nut (19) is preferably used to secure the connection between the body (21) and the adapter (22). Downstream from the column (2), the body (21) is connected to an adapter (23) that reduces the internal diameter between the body (21) of the column (2) and the tube (14). The tube (13) directs the eluant into the column (2) and the tube (14) exits the eluate outside the column (2). Preferably, the tube (14) has a J-shape so that both tubes (13, 14) go in and out the generator (1) upwardly as illustrated in FIG. 1. Preferably, the tube (13) has a S-shape so that both tubes (13, 14) are sufficiently spaced apart.

In accordance with an embodiment of the invention, which is illustrated in FIGS. 2 and 3, the tubes (13, 14) are connected to their respective lines by means of a quick connect, respectively. The female part (16) of a quick connect is illustrated in connection with the tube (13), and the male part (17) of a quick connect is illustrated in connection with the tube (14). In FIG. 2, the tube (13) and the adapter (22) are disconnected with the column (2) by unscrewing the nut (19). As shown in FIG. 3, when unscrewed, the nut (19) can freely slide along the body (21) of the column (2) so as to expose the inlet port (10). This allows the filling port (18) to be fixed on the inlet port (10) so as to fill the column with the matrix.

According to an embodiment of the invention, the depyrogenation preferably consists in dry heating at a temperature of at least 210° C. for a period of at least 3 hours, or at a temperature from about 210° C. to about 280° C. for a period that is from 3 hours to 12 hours, or at a temperature of about 260° C. ±5° C. for a period that is from 3 hours to 6 hours.

According to an embodiment of the invention, the sterilization preferably is performed as disclosed below.

According to an embodiment of the invention, the particulate ion exchange matrix comprises alpha-stannic acid, zirconium oxide, titanium oxide, aluminum oxide, silica gel, other inorganic, organic ion exchange matrices, or any combination thereof. The particulate ion exchange matrix is preferably alpha-stannic acid.

According to an embodiment of the invention, the particulate ion exchange matrix has a particle size of about 50 µm to about 200 µm, and preferably of about 75 µm to about 150 µm. In order to obtain the desired size of particle, a two-tier sieve is used.

According to an embodiment of the invention, the parent radioisotope comprises preferably strontium-82, and the radioisotope comprises preferably rubidium-82.

According to an embodiment of the invention that is illustrated in the figures, the column (2) has an inlet (10) (also called inlet port), a body (21), and an outlet (11) (also called outlet port); and the body (2) has a length of about 3.0 cm to about 8.0 cm, an internal diameter of about 4 mm to about 12 mm, and a wall that has a thickness of about 0.4 mm to about 1.2 mm. According to another embodiment, the body (21) of the column (2) has a length of about 4.0 cm to about 8.0 cm, an internal diameter of about 5 mm to about 7 mm, and a wall having a thickness of about 0.4 mm to about 0.6 mm.

According to another embodiment of the invention, the column is prepared by including an additional step that comprises a phosphoric acid treatment of the column. Phosphoric acid treatment is used as a chemical-cleaning agent for stainless steels but is not considered to be a "passivating" acid. The phosphoric acid treatment is performed on an empty column. The phosphoric acid treatment preferably comprises soaking the column in a phosphoric acid solution that has a concentration of about 5% to 85%.

According to another embodiment of the invention, the column is prepared by including an additional step of performing a passivation treatment of the column, when the column is empty. The passivation treatment preferably comprises soaking the column in a nitric acid solution, a solution with nitric acid and sodium dichromate, or a citric acid solution. Passivation maximizes the inherent corrosion resistance of a stainless alloy.

According to another embodiment of the invention, the column is preferably installed in a generator compartment, before above-mentioned step (c). Said generator compartment is preferably made of a radiation resistant material and a heat resistant material. The generator material preferably comprises stainless steel, titanium, tin, nickel, cadmium, tungsten, tin, copper, aluminum, lead, or a combination thereof. The generator compartment together with the column installed therein can be advantageously sterilized prior to be used in order to add a sterilization step after the column is being loaded with the matrix. This additional sterilization step may also be performed after the column was stored and prior to charging the parent radioisotope thereon. The sterilization is performed with steam under a pressure of at least about 15 psi, and at a temperature from about 110° C. to about 150° C., or at about 121° C., for a period of about 20 minutes to about 60 minutes, or at least 20 minutes, or from about 20 minutes to about 30 minutes. The sterilization is preferably performed in a saturated steam environment. The sterilization is preferably performed under a pressure of about 15 psi to about 45 psi, and preferably about 28 psi to about 33 psi, and preferably about 30 psi to about 32 psi.

The ability of the generator and the column installed therein to be sterilized prior to use allows the column preparation steps such as the steps of loading the particulate ion exchange matrix in the column and charging the parent radioisotope on the matrix to be performed in a non-sterile environment.

According to another embodiment of the invention, the column is reusable. As such, after being used in an elution system for eluting the radioisotope, the used column may undergo a cleaning process, which includes the following steps:

a) emptying the used column by removing the used matrix therefrom;

b) sterilizing the empty column of step (a); and c) loading a new particulate ion exchange matrix into the sterilized column of step (b).

The sterilization during the cleaning process is preferably performed in a similar manner as the above-mentioned sterilization for the generator compartment and column.

FIG. 1 is a schematic diagram of an embodiment where a generator column (2) is combined with an elution system. In this embodiment, an eluant reservoir (8), wherein the eluant is preferably a saline solution, provides the eluant to the column (2) by means of an eluant line 3, and the eluant is pushed into the eluant line (3) by means of a pump (9). In this embodiment, the outlet port (11) is connected through the outlet line (12) to a valve (7). The valve (7) may direct the flow of eluate to the patient line (6) and the waste line (4) up to the waste reservoir (5). The generator (1) has a cover (15), which is preferably shielded to prevent the escape of radiation from the generator (1).

FIG. 2 shows an embodiment of the column (2) where the inlet of the column (2) is securely connected to an adapter (22) by means of nut (19). The adapter (22) is preferably connected to a S-shaped tube, which ends with a quick connect. Only the female part (16) of said quick connect is shown in FIG. 2. In the embodiment of FIG. 2, the column (2) has an outlet that is securely connected to an adapter (23) by means of nut (20). The adapter (23) is preferably connected to a J-shaped tube that extends upwardly and ends with a quick connect. Only the male part (17) of this quick connect is shown in FIGS. 2 and 3.

FIG. 3 is a representation of an embodiment of the column (2) wherein the column (2) is ready for loading. In particular, it can be noted that the S-shape tube (13) and the adapter (22) are disconnected from the column (2) and the nut 19 may freely slide along the body (21) of the column (2). After disconnecting the nut 19, the inlet port (10) is rendered accessible. According to an embodiment, a filling port (18) is installed on the inlet port so as to direct the particle ion exchange matrix inside inlet port (10) of the column (2) and facilitate filling the column (2). The filling port (18) may have various shape such a tube, a funnel or else. In a preferred embodiment, the filling port (18) is made of silicone and fits tightly on the inlet port (10).

EXAMPLE

Example 1—Loading Procedure

The loading procedure may be performed as follows:
1. Sieve about 7 g of particles to the appropriate size (75-150 μm).
2. Place the appropriately sized particles into a 100 mL beaker.
3. Add 10 mL of the rinsing solution.
4. Swirl and allow to settle for 5 seconds, and then decant immediately.
5. Repeat 7× the sequence of steps 3 and 4.
6. Place a 5 cm sterile silicone tube (called "the filling port" herein) onto the top of the inlet port of the column to be packed.
7. Pour the rinsing solution up to about 1 cm from the top of the silicone tube.
8. Add the rinsed matrix resulting from step 5 with spatula until the silicone tube is full.
9. Tap ten times the column with approximately 1 joule of force.
10. Remove rinsing buffer until the rinsing buffer reaches the level of about 1 cm from the top of the silicone tube.
11. Repeat the sequence of steps 8-10 until the level of matrix reaches the inlet port of the column.

The present invention contemplates any combination of the embodiments and the preferred elements described therein. For conciseness, every combination is not recited therein although every combination is contemplated herein by the inventors and is thus encompassed by the present disclosure. While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

What is claimed:

1. A generator column of an elution system for the elution of a radioactive solution, wherein the column is prepared by the following steps:
   a) a pre-loading step that is performed prior to loading the column with charged matrix, which comprises loading the column partially with a particulate ion exchange matrix at about 50% to 85% of the total capacity of the column that is not charged with a parent radioisotope;
   b) performing the completion of column loading by charging the remaining amount of matrix with the parent radioisotope outside the column; and
   c) loading the charged matrix in the column.

2. The generator column of claim 1, wherein the charging of matrix with the parent radioisotope is performed by eluting a solution of parent radioisotope at a flow rate from about 0.5 mL/h to about 5.0 mL/h.

3. The generator column of claim 1, wherein the parent radioisotope is strontium-82 and the desired radioisotope is rubidium-82.

4. The generator column of claim 1, wherein the column is charged with the parent radioisotope at a flow rate of about 1 mL/h.

5. The generator column of claim 1, wherein charging the parent radioisotope on the matrix is performed in a non-sterile environment.

6. A generator column of an elution system for the elution of a radioactive solution, wherein the column is cleaned following use by a process comprising the following steps:
   a) emptying the used column by removing the used matrix therefrom;
   b) optionally, sterilizing the empty column resulting from step (a);
   c) loading a new particulate ion exchange matrix into the sterilized column resulting from step (b);
   d) charging a parent radioisotope on the particulate ion exchange matrix of step (c), and
   e) sterilizing e charge column.

7. The generator column of claim 6, wherein the process further comprises the steps of:
   a) a conditioning step, and
   b) a rinsing step.

8. The generator column of claim 7, wherein the conditioning step is performed by using 2M sodium chloride at a flow rate of about 0.5 mL/min.

9. The generator column of claim 7, wherein the rinsing step is performed by using 0.9% sodium chloride at a flow rate of about 10 mL/min.

10. The generator column of claim 6, wherein the particulate ion exchange matrix comprises alpha-stannic acid, zirconium oxide, titanium oxide, aluminum oxide, silica gel, other inorganic, organic ion exchange matrices, or any combination thereof.

11. The generator column of claim 6, wherein the generator column is installed into a generator compartment, and the generator compartment and the column installed therein are sterilized.

12. The generator column of claim 6, wherein the sterilization of the empty column is performed with steam at a temperature from about 110° C. to about 150° C., for a period is from about 20 minutes to about 60 minutes.

13. The generator column of claim 6, further comprising a step of performing a phosphoric acid treatment of the column.

14. The generator column of claim 6, further comprising a step of performing a passivation treatment of the column.

15. The generator column of claim 6, wherein the generator column further comprises the step of:
   a) washing the ion exchange matrix, and
   b) packing the ion exchange matrix of step (a) in the said generator column.

16. The generator column of claim 15, wherein the ion exchange matrix is washed with a buffer solution or an ionic solution or a solution with a basic pH.

17. The generator column of claim 16, wherein the solution is ammonium hydroxide and ammonium chloride buffer, a solution of ammonium hydroxide or a solution of sodium hydroxide.

18. The generator column of claim 6, wherein the charging of matrix with the parent radioisotope is performed by eluting a solution of parent radioisotope at a flow rate from about 0.5 mL/h to about 5.0 mL/h.

19. The generator column of claim 6, wherein the parent radioisotope is strontium-82 and the desired radioisotope is rubidium-82.

20. The generator column of claim 6, wherein charging the parent radioisotope on the matrix is performed in a non-sterile environment.

* * * * *